(12) United States Patent
Viswanathan et al.

(10) Patent No.: US 8,359,106 B2
(45) Date of Patent: Jan. 22, 2013

(54) COLD PLASMA BONDING OF POLYMERIC TUBING IN IMPLANTABLE MEDICAL DEVICES

(75) Inventors: Kalpana Viswanathan, St. Paul, MN (US); Paul E. Zarembo, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 804 days.

(21) Appl. No.: 12/557,375

(22) Filed: Sep. 10, 2009

(65) Prior Publication Data
US 2010/0125318 A1    May 20, 2010

Related U.S. Application Data

(60) Provisional application No. 61/114,661, filed on Nov. 14, 2008.

(51) Int. Cl.
*A61N 1/04* (2006.01)
*B05D 5/10* (2006.01)

(52) U.S. Cl. .................. 607/116; 427/539; 427/2.31

(58) Field of Classification Search .................. 607/115, 607/116, 119, 156
See application file for complete search history.

(56) References Cited

U.S. PATENT DOCUMENTS

| | | |
|---|---|---|
| 4,131,691 A | 12/1978 | Morley et al. |
| 4,261,806 A | 4/1981 | Asai et al. |
| 4,312,693 A | 1/1982 | Salensky et al. |
| 4,488,954 A | 12/1984 | Hatada et al. |
| 4,632,842 A | 12/1986 | Karwoski et al. |
| 4,656,083 A | 4/1987 | Hoffman et al. |
| 4,868,096 A | 9/1989 | Nakayama et al. |
| 5,034,265 A | 7/1991 | Hoffman et al. |
| 5,132,108 A | 7/1992 | Naarayanan et al. |
| 5,244,654 A | 9/1993 | Naarayanan |
| 5,364,662 A | 11/1994 | Domenico et al. |
| 5,409,696 A | 4/1995 | Naarayanan et al. |
| 5,451,428 A | 9/1995 | Rupp |
| 5,486,357 A | 1/1996 | Naarayanan |
| 5,591,140 A | 1/1997 | Naarayanan et al. |
| 5,876,753 A | 3/1999 | Timmons et al. |

(Continued)

FOREIGN PATENT DOCUMENTS

GB    2207391 A    2/1989

(Continued)

OTHER PUBLICATIONS

Chaudhury, M.K. et al., "Direct Measurements of Interfacial Interactions Between Semispherical Lenses and Flat Sheets of Poly(dimethylsiloxane) and Their Chemical Derivatives", *Langmuir* 1991, 7, 1013-1025.

(Continued)

*Primary Examiner* — Carl H Layno
*Assistant Examiner* — Erin Piateski
(74) *Attorney, Agent, or Firm* — Faegre Baker Daniels LLP

(57) ABSTRACT

Adhesiveless direct bonding between polymeric tubular members assembled with an interference fit using an oxidative cold gas plasma treatment, and implantable medical leads manufactured in part using a cold gas plasma bonding process are disclosed. An illustrative method includes subjecting a number of polymeric tubular members to an oxidative cold gas plasma, creating an oxygen rich layer on each of the tubular members. The treated surfaces of the tubular members are assembled together, forming a direct bond along an overlapping region between the tubular members when in conformal contact with each other.

22 Claims, 5 Drawing Sheets

U.S. PATENT DOCUMENTS

| | | | |
|---|---|---|---|
| 6,021,355 | A | 2/2000 | Shchervinsky |
| 6,299,596 | B1 | 10/2001 | Ding |
| 7,396,582 | B2 * | 7/2008 | Claude et al. ................ 428/220 |
| 7,423,234 | B2 | 9/2008 | Dumont et al. |
| 2004/0215300 | A1 | 10/2004 | Verness |
| 2006/0089695 | A1 | 4/2006 | Bolea et al. |
| 2007/0051531 | A1 * | 3/2007 | Borgaonkar et al. ...... 174/126.1 |
| 2008/0221509 | A1 * | 9/2008 | Gottlieb et al. ................ 604/43 |
| 2009/0048652 | A1 * | 2/2009 | Malik et al. .................. 607/116 |

FOREIGN PATENT DOCUMENTS

| | | | |
|---|---|---|---|
| WO | 2008119387 | A1 | 10/2008 |

OTHER PUBLICATIONS

Duffy, D.C. et al., "Rapid Prototyping of Microfluidic Systems in Poly(dimethylsiloxane)", *Anal. Chem.* 1998, 70, 4974-4984.

Schueller, O.J.A. et al., "Reconfigurable Diffraction Gratings Based on Elastomeric Microfluidic Devices", *Sensor Actuator*, 1998, 78, 149-159.

Duffy, D.C. et al., "Rapid Prototyping of Microfluidic Switches in Poly(dimethylsiloxane) and Their Actuation by Electro-Osmotic Flow", *Micromechan. Microeng.*, 1999, 9, 211-217.

McDonald, J.C. et al., "Fabrication of Microfluidic Systems in Poly(dimethylsiloxane)", *Electrophoresis*, 2000, 21, 27-40.

Bhattacharya, Shantanu, "Plasma Bonding of Poly(dimethyl) Siloxane and Glass Surfaces and its Application to Microfluidics", A Thesis in Mechanical Engineering, Submitted to the Graduate Faculty of Texas Tech University, Dec. 2003.

Nazmul Huda Al Mamun, "Patterning of Platinum Microelectrodes in Polymeric Microfluidic Chips", *J. Microlith., Microfab., Microsyst.*, Jul.-Sep. 2006/vol. 5(3), pp. 1-6.

International Search Report and Written Opinion issued in PCT/US2009/056548, mailed Feb. 3, 2010, 14 pages.

\* cited by examiner

COLD PLASMA BONDING OF POLYMERIC TUBING IN IMPLANTABLE MEDICAL DEVICES

CROSS-REFERENCE TO RELATED APPLICATION

This application claims priority under 35 U.S.C. §119 to U.S. Provisional Application No. 61/114,661, filed on Nov. 14, 2008, entitled "Cold Plasma Bonding of Polymeric Tubing in Implantable Medical Devices," which is incorporated herein by reference in its entirety for all purposes.

TECHNICAL FIELD

The present invention relates generally to the direct bonding of tubular members. More specifically, the present invention relates to the direct bonding of polymeric tubular members by gas plasma surface modification, and to implantable medical leads manufactured in part using a cold gas plasma bonding process.

BACKGROUND

Implantable medical devices such as pacemakers and cardiac defibrillators often employ leads that are used to provide therapy to a patient and/or to sense various parameters within a patient's body. An implantable cardiac defibrillator lead, for example, may include a flexible lead body tube containing a number of exposed electrodes for providing stimulus energy to a desired location within the patient's heart. In some cases, an outer tube may be placed over portions of the lead body to provide the lead with a desired physical characteristic during implantation of the lead within the body. In implantation techniques using a hemostatic introducer to percutaneously insert the lead into the body, for example, an outer tube placed over the lead body can be used to facilitate insertion and subsequent removal of the lead within the interior lumen of the introducer.

In some designs, the various components of the lead, including the lead body tube and outer tube, are fabricated using a number of polymeric members that are assembled together and bonded to each other during manufacturing. Typically, the polymeric materials used in the construction of the lead are selected so as to meet various design specifications, including lead flexibility, radial and longitudinal strength, reliability, and biocompatibility. In some cases, more than one polymeric material is used to provide the desired combination of lead properties.

A number of different techniques have been employed for bonding polymeric and other lead members together, including adhesive bonding, thermal bonding, and chemical bonding. Many of these techniques, however, require specific material combinations, and in some cases can result in a change in the desired physical characteristics of the lead itself. In an adhesive technique, for example, the adhesives used may have limitations regarding the substrate combinations that can be bonded together, and may require additional steps such as the use of primers or surface activation to achieve reliable bonding. Another issue with adhesive techniques is that the application area of the adhesive may be limited. In some cases, for example, the adhesive bonds may be formed at only certain locations along the length of the lead, which can cause bunching between the outer tube and the lead body. Such bunching can occur, for example, when the lead is inserted into and subsequently removed from the introducer used for inserting the lead into the body, which exerts a force on the outer tube that causes the outer tube to move relative to the lead body tube. In some cases, the bunching can result in increased stress on the adhesive bonds between the outer tube and the lead body tube as well as increased stress on other bonds such as those used to secure the electrodes to the lead body tube.

SUMMARY

The present invention relates to plasma bonding polymeric tubular members together, where one or both tubular members are silicone containing elastomers and are in an interference fit with each other. The present invention also relates to implantable medical leads manufactured in part using a cold gas plasma bonding process. An illustrative method of manufacturing a medical device lead includes providing a first silicone tubular member and a second silicone tubular member, subjecting an inner surface of at least a portion of the first silicone tubular member to an oxidative cold gas plasma treatment for a first period of time, subjecting an outer surface of at least a portion of the second silicone tubular member to an oxidative cold gas plasma treatment for a second period of time, and assembling the first silicone tubular member over the second silicone tubular member. When subjected to the cold gas plasma treatment, an oxygen rich layer is formed on each of the tubular members which, when assembled together, forms a direct bond along an overlapping region between the members.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
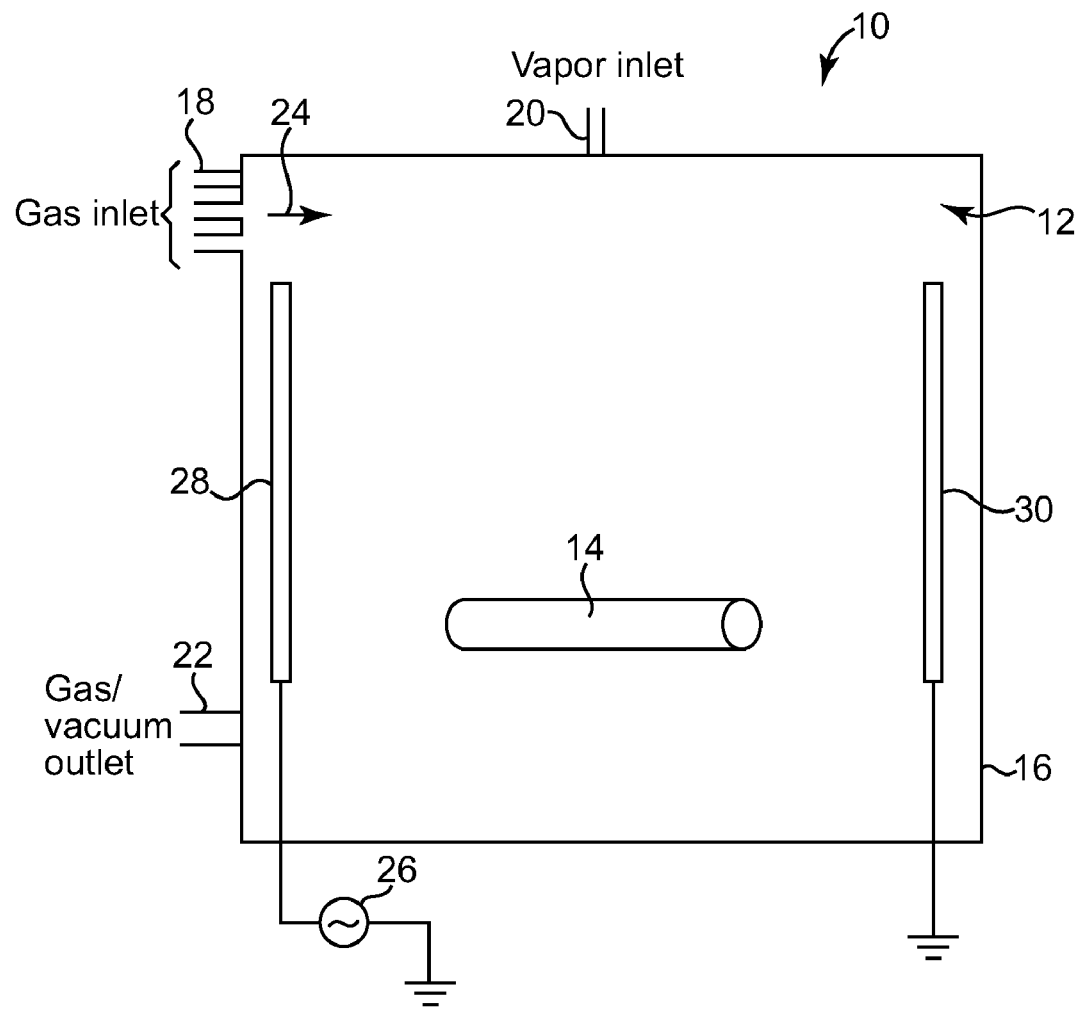
FIG. 1 is a diagrammatic view of a cold gas plasma apparatus for generating an oxidative plasma suitable for surface treating a polymeric member used in the manufacturing of a medical device.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a diagrammatic view of an illustrative cold gas plasma apparatus 10 for generating an oxidative plasma suitable for surface treating a tubular member used in the manufacturing of a medical device. In certain embodiments, for example, the apparatus 10 may be used to surface treat a lead body tube and outer tube used in manufacturing a medical device lead such as the cardiac defibrillator lead described further herein with respect to FIGS. 3-5. Alternatively, and in other embodiments, the apparatus 10 can be used to surface treat other medical lead components, or can be used to surface treat other medical devices in which direct bonding between two or more members is desired. In some embodiments, the apparatus 10 may comprise a gas treatment apparatus similar to that described in commonly owned U.S. Pat. No. 6,299, 596, entitled "Method of Bonding Polymers and Medical Devices Comprising Materials Bonded By Said Method," the contents of which is incorporated herein by reference in its entirety.

As shown in FIG. 1, the apparatus 10 includes a gas plasma treatment system 12 that can be used to subject one or more polymeric lead components 14 to an oxidative gas plasma that chemically modifies an exposed surface of each component 14, producing a thin, oxygen rich layer or coating that can be used to enhance the bonding of the component 14 to another treated component. The system 12 includes a treatment chamber 16 operationally coupled to a gas inlet 18, a vapor inlet 20, and a gas/vacuum outlet 22. The gas inlet 18 provides an oxidative gas 24 to the interior of the treatment chamber 16. In certain embodiments, the oxidative gas 24 includes pure oxygen or oxygen contained in air. Alternatively, and in other embodiments, the oxidative gas 24 is a mixture of oxygen and one or more non-reducible gases such as argon or nitrogen. While an oxidative gas 24 may be provided within the treatment chamber 16 to chemically modify and treat the surface of the lead component 14, other gasses suitable for chemically modifying and treating the surface of the component 14 are also possible. In one alternative embodiment, for example, an acrylic acid or an ammonia methane gas plasma may be generated within the treatment chamber 16 for treating the component 14.

The gas plasma treatment system 12 further includes an energy source 26 adapted to supply energy to a number of electrodes 28,30 sufficient to ionize at least a portion of the oxidative gas 24 at or near ambient temperatures to form a cold gas plasma within the treatment chamber 16. Example energy sources 26 suitable for generating gas plasma can include, but are not limited to, radio frequency (RF) energy sources, direct current (DC) energy sources, and microwave energy sources. An example RF energy source capable of ionizing the oxidative gas 24 and generating gas plasma at or near ambient temperatures may supply power to the treatment chamber 16 in the range of between about 35 Watts to 1000 Watts. Other RF energy sources having power ratings greater or lesser than this range are possible, however, depending on the pressure and temperature within the treatment chamber 16, the composition of the oxidative gas 24, the type and amount of any non-reducible agents contained within the treatment chamber 16, the size of the treatment chamber 16, as well as other factors.

Figure 2:
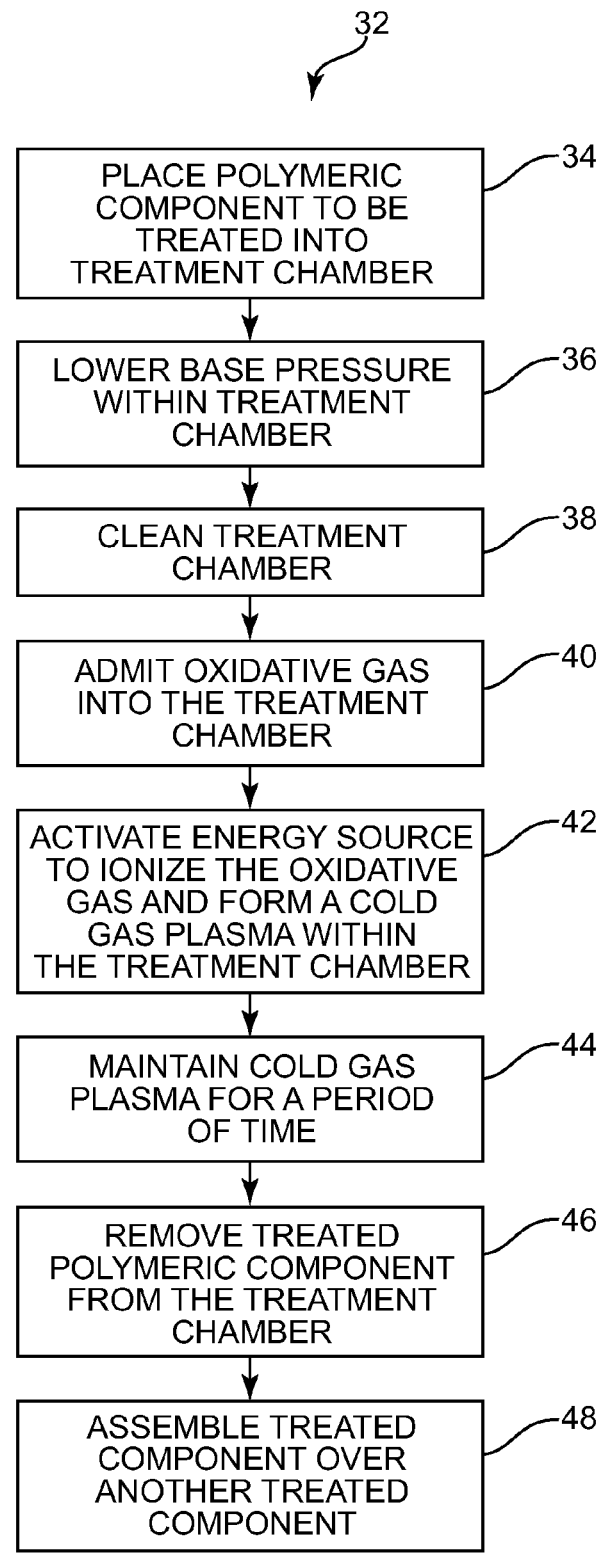
FIG. 2 is a flow chart showing an illustrative method of surface treating a polymeric tubular member using the cold gas plasma apparatus of FIG. 1.

FIG. 2 is a flow chart showing an illustrative method 32 of surface treating a polymeric tubular member using the cold gas plasma apparatus 10 of FIG. 1. As shown in FIG. 2, the method 32 can begin generally at block 34 in which a polymeric component 14 to be treated is placed within the treatment chamber 16. In certain embodiments, for example, the polymeric component 14 may comprise a silicone tubular member used in constructing a lead body tube or outer tube of a medical lead. Alternatively, and in other embodiments, the polymeric component 14 may comprise another component of a medical lead, or a component from another medical device to be treated.

Once the component 14 is inserted into the treatment chamber 16 (block 34), the base pressure within the treatment chamber 16 can be lowered to a pressure below atmospheric pressure (e.g., 20 mTorr) (block 36). The treatment chamber 16 can then be cleaned (block 38) by flowing a non-reactive gas such as nitrogen, argon, helium, or mixtures thereof through the chamber 16 for a period of time sufficient to remove any impurities within the chamber 16. The oxidative gas 24 is next admitted into the treatment chamber 16 (block 40), and the energy source 26 activated to ionize at least a portion of the gas 24 to form a cold gas plasma within the chamber 16 (block 42). In some embodiments, for example, the oxidative gas 24 can be admitted into the treatment chamber 16 at a flow rate of about 70 sccm to about 200 sccm and subjected to RF energy in the range of between about 35 Watts to 150 Watts for a period of time sufficient to chemically modify the surface of the component 14 or portions thereof.

The process of energizing the oxygen gas 24 and creating gas plasma within the treatment chamber 16 can be maintained for a period of time (block 44) sufficient to produce an oxygen rich layer on the component 14 but without affecting the bulk properties of the material. The time required to surface treat the component 14 will typically vary depending on the particular component to be treated so as to obtain an optimally modified surface without over oxidizing the surface. In some embodiments, X-ray photoelectron spectroscopy (XPS) can be used to analyze the surface chemistry of the treated component 14 to determine whether the component 14 has an optimally modified surface.

In the treatment of an outer surface of a silicone tubular member 14 used in fabricating a lead body tube, the treatment time required to produce an oxygen rich layer on the member 14 will typically take about 30 seconds to 2 minutes, and more specifically, about 1 minute. In the treatment of an interior surface of a silicone tubular member 14 used in fabricating an outer tube, in contrast, the treatment time required to produce an oxygen rich layer on the inner surface will typically take about 5 to 15 minutes, and more specifically, about 10 minutes. The times required to surface treat the two silicone members 14 may vary, however, depending on the flow rate of the oxygen gas 24, the power provided by the energy source 26, the size and composition of the members 14 being treated, the pressure within the treatment chamber 16, as well as other factors. In some embodiments, capillary rise measurements can be utilized to determine whether the treatment times are sufficient to produce oxygen rich layers on the treated members 14. An example method of performing capillary rise measurements on a surface treated member is described, for example, in U.S. Pat. No. 5,486,357, entitled "Radiofrequency Plasma Biocompatibility Treatment of Inside Surfaces," the contents of which is incorporated herein by reference in its entirety.

When subjected to the cold gas plasma treatment, the oxidative gas 24 within the treatment chamber 16 produces an oxygen rich layer containing silanols on the exposed portions of the polymeric member 14, including the exterior surface and interior luminal surface of the member 14. Once treated, the polymeric member 14 may then be removed from the treatment chamber 16 (block 46) and then immediately assembled over another treated member (block 48) such that the outer tubular member is in compression over the inner tubular member (e.g., via an interference fit of between about two thousandths of an inch to ten thousandths of an inch), causing the two polymeric members to directly bond to each other along an overlapping region of the two members without the application of an external force or bonding agent. In some embodiments where the tubular members are assembled together via an interference fit, plasma modification of the member 14 is performed under atmospheric conditions to produce the direct bond. Alternatively, and in other embodiments, the plasma modification of the member 14 is performed at a reduce temperature and/or pressure to produce the direct bond.

Figure 3:
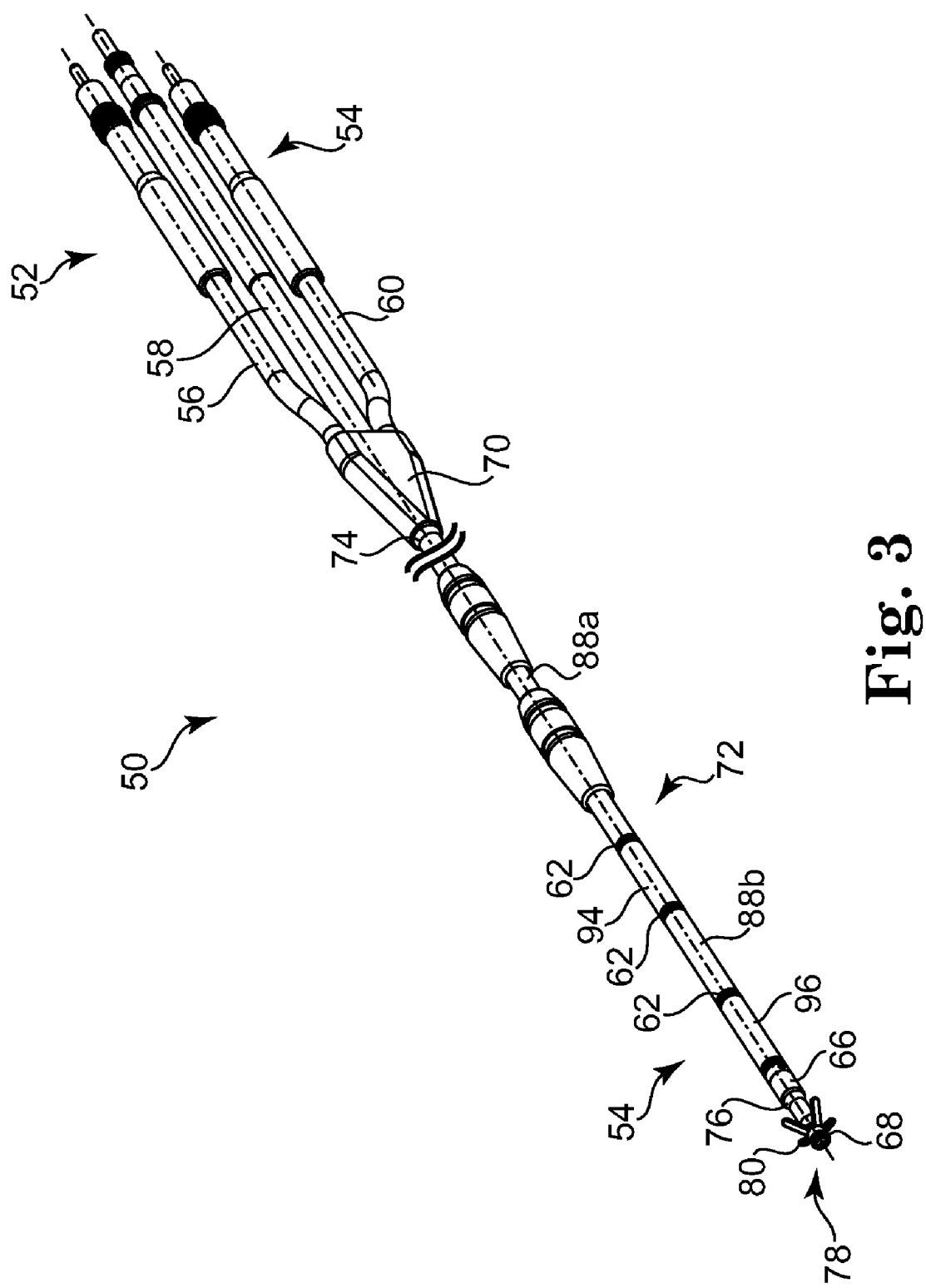
FIG. 3 is a perspective view of an implantable medical lead in accordance with an illustrative embodiment including several silicone tubular members bonded together after being subjected to a gas plasma surface treatment.

FIG. 3 is a perspective view of an implantable medical lead 50 in accordance with an illustrative embodiment including several silicone tubular members bonded together after being subjected to a cold gas plasma surface treatment. The medical lead 50, illustratively a cardiac defibrillator lead, includes a proximal section 52 and a distal section 54. The proximal section 52 of the lead 50 includes a connector assembly 54 including a number of tubular sleeves 56,58,60 each containing an electrical conduit that provides electrical energy to a number of shocking coils 62 and electrodes 66,68 located on the distal section 54 of the lead 50. The connector assembly 54 can be connected to an implantable pulse generator (not shown), which supplies currents to the shocking coils 62 and electrodes 66,68 to provide a desired therapy to the patient's heart and/or to sense electrical activity occurring within the body.

A silicon yoke 70 on the proximal section 52 of the lead 50 couples the connector assembly 54 to a tubular lead body 72. The lead body 72 extends distally from a first end 74 located at or near the yoke 70 to a second end 76 located at or near the distal end 78 of the lead 50. The second end 76 of the lead body 72 terminates at a lead tip 80, which can be used to secure the distal end 78 of the lead 50 to the patient's heart.

Figure 4:
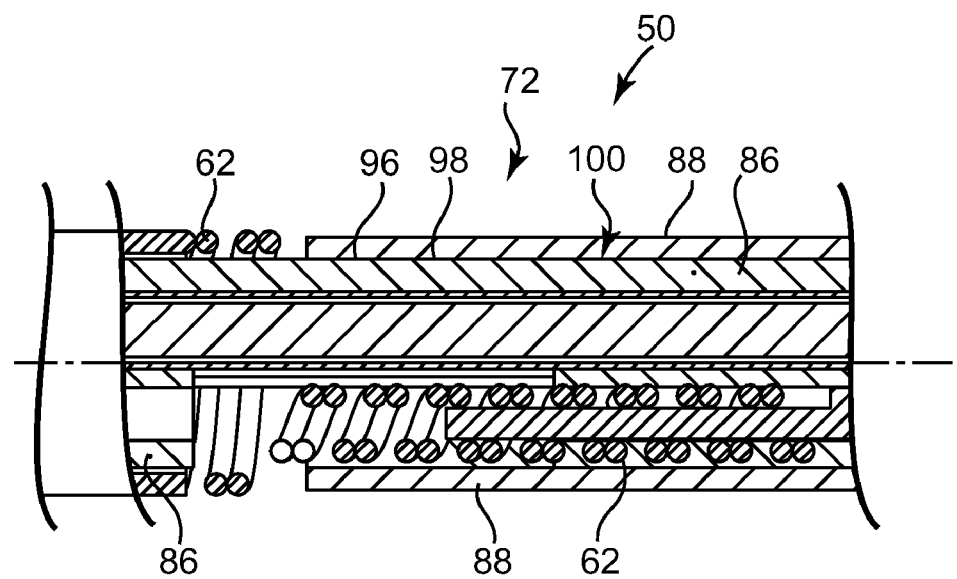
FIG. 4 is a partial, longitudinal cross-sectional view of a portion of the lead body of FIG. 3.

FIG. 4 is a partial, longitudinal cross-sectional view of a portion of the lead body 72 of FIG. 3, showing the interior of the lead body 72 in greater detail. FIG. 4 may represent, for example, a view of the interior of the lead 50 at an exposed portion of one of the shocking coils 62. As further shown in FIG. 4, the lead body 72 can include an inner silicone tubular member 86 and a number of outer silicone tubular members 88 directly bonded about the inner silicone tubular member 86 using a cold gas plasma bonding method, as described in further detail herein. In some embodiments, the inner tubular member 86 may extend continuously along all or a substantial portion of the length of the lead body 72.

The outer tubular members 88 may overlap the inner tubular member 86 at various locations along the length of the lead body 72. In certain embodiments, and as shown in FIG. 3, a proximal outer tubular member 88a may overlap a first portion of the lead body 72. A second outer tubular member 88b, in turn, may overlap a second portion of the lead body 72 distal to the first outer tubular member 88a. In other embodiments, other outer tubular members may be placed at other locations along the length of the lead body 72, depending on the configuration of the lead 50. In use, the outer tubular members 88a,88b provide the lead 50 with a substantially uniform profile along the length of the lead body 72.

The inner and outer tubular members 86,88 may each comprise a biocompatible polymer adapted to impart a desired physical characteristic to the lead 50. In certain embodiments, for example, the inner and outer tubular members 86,88 may each comprise a biocompatible elastomer such as silicone rubber. In some embodiments, the exterior surface of the member 88 can be made lubricious to reduce slippage within the body resulting from patient body movements and cardiac-induced movement of the lead 50.

Figure 5:
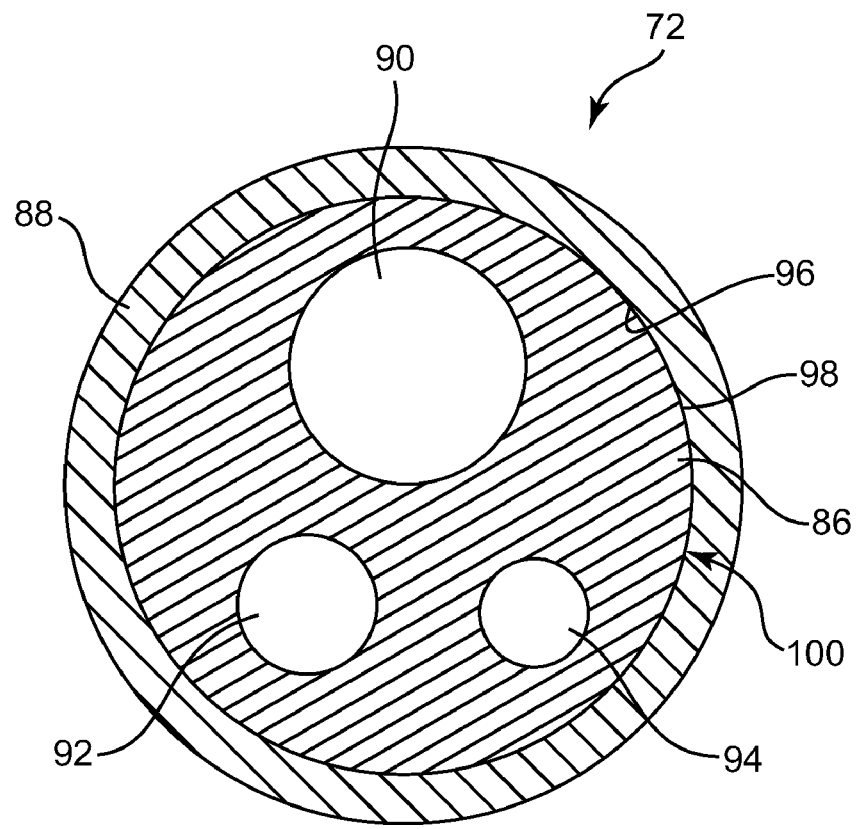
FIG. 5 is a transverse cross-sectional view of the lead body of FIG. 3 showing the bonding of the inner tubular member to the outer tubular member.

FIG. 5 is a transverse cross-sectional view of the lead body 72 showing the bonding of the inner tubular member 86 to the outer tubular member 88. As further shown in FIG. 5, the inner tubular member 86 may include a number of internal lumens 90,92,94 that house a number of electrical conductors (not shown) for supplying current to the shocking coils 62 and electrodes 66,68. For illustrative purposes, the three lumens 90,92,94 of the inner tubular member 86 are shown having different diameters. In other embodiments, however, the relative dimensions of the lumens 90,92,94 may vary from that shown. In addition, the inner tubular member 86 may include a greater or lesser number of lumens, depending on the particular configuration of the lead 50. For example, the inner tubular member 86 may include a greater number of lumens to house additional conductor wires and/or electrode coils within the lead 50 for supplying current to other shocking coils and/or pace/sense electrodes.

During fabrication of the lead 50, the outer surface 96 of the inner tubular member 86 and the inner surface 98 of the outer tubular member 88 can each be subjected to a cold gas plasma surface treatment, forming oxygen rich layer on each of the surfaces 96,98. In certain embodiments, for example, each of the inner tubular member 86 and the outer tubular member 88 can be surface treated with a cold gas plasma using the treatment method 32 described above with respect to FIG. 2.

When the outer tubular member 88 is inserted over the inner tubular member 86 during assembly such that the outer tubular member 88 is in compression over the inner tubular member 86 (e.g., via an interference fit), the oxygen rich layers formed on each of the surfaces 96,98 react and directly bond with each other along an overlapping region 100 between the members 86,88. In some embodiments, the inner and outer tubular members 86,88 can be treated such that an oxygen rich layer is formed along all or a substantial portion of the overlapping region 100 between the assembled members 86,88. When provided along all or a substantial portion of the overlapping region 100, the plasma surface treatment results in a direct bond between the two members 86,88 along their length. In contrast to other techniques such as adhesive bonding where the adhesive bonds are typically placed at discrete locations along the overlapping region, the direct bonding process utilizing a gas plasma treatment results in fusion along substantially the entire length between the overlapping region 100 of the two members 86,88. As a result, the outer tubular member 88 is less susceptible to bunching over the inner tubular member 86.

Figure 6:
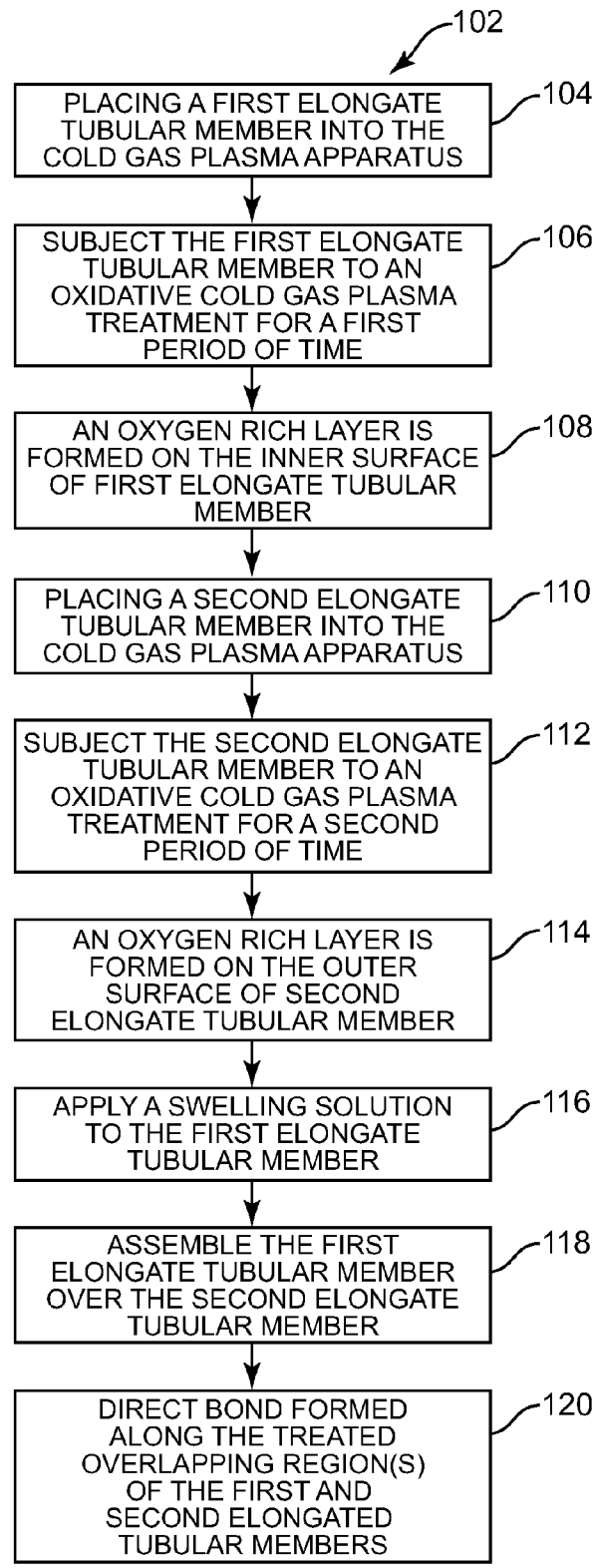
FIG. 6 is a flow chart showing a method of manufacturing a medical device lead in accordance with an illustrative embodiment.

FIG. 6 is a flowchart showing a method 102 of manufacturing a medical device lead in accordance with an illustrative embodiment using the cold gas plasma apparatus 10 of FIG. 1. The method 102 of FIG. 6 may represent, for example, several steps that can be used to fabricate the medical lead 50 of FIGS. 3-5. Although the illustrative method 102 is described in conjunction with medical device 50, in other embodiments the method 102 can be employed in fabricating other medical device leads, or in fabricating other medical devices in which two or more polymeric members are bonded together.

As shown in FIG. 6, the method 102 may begin generally at block 104 by placing a first elongate tubular member (e.g., outer tubular member 88) into the treatment chamber 16 of the cold gas plasma apparatus 10. Once inserted, the outer tubular member 88 is exposed to an oxidative cold gas plasma within the treatment chamber 16 for a first period of time (block 106). In certain embodiments, for example, the outer tubular member 88 is subjected to a gas plasma treatment for a period of about 5 minutes to about 15 minutes, and more specifically, about 10 minutes. When exposed to the oxidative gas plasma, an oxygen rich layer is formed on the exposed surfaces of the tubular member 86, including the inner surface 98 of the member 88 (block 108). The time required for treating the outer tubular member 88 is typically greater than the time required to treat the inner tubular member 86 in order to ensure satisfactory modification of the interior surface 98 with an oxygen rich layer.

A second elongate tubular member (e.g., the inner tubular member 86) can be inserted into the treatment chamber 16 of the gas plasma apparatus 10 (block 110), and subjected to an oxidative cold gas plasma for a second period of time (block 112). In certain embodiments, for example, the inner tubular member 86 is subjected to a gas plasma treatment for a period of about 30 seconds to about 2 minutes, and more specifically, about 1 minute. When exposed to the oxidative gas plasma, an oxygen rich layer is formed on the exposed surfaces of the inner tubular member 86, including the outer surface 96 of the member 86 (block 114).

The time required to produce the oxygen rich layers on each of the tubular members 86,88 will typically vary depending on the dimensions of the members 86,88 as well as the operational characteristics of the apparatus 10, including the composition and flow rate of the oxidative gas 24 and the amount of energy supplied by the energy source 26. For example, for a given flow rate and supply of energy, the time required to form an oxygen rich layer on the inner surface 98 of the outer tubular member 88 will typically increase as the inner diameter of the member 88 decreases. The time required to generate the oxygen rich layer on the inner surface 98 of the outer tubular member 88 may also be affected by the length of the member 88.

Once each of the tubular members 86,88 to be bonded together are treated within the treatment chamber 16, an assembly process can then be performed to assemble the outer tubular member 88 over the inner tubular member 86. In some embodiments, the process of assembling the members 86,88 together will be performed immediately after the treatment process, prior to the degradation of the oxygen rich layers formed on the surfaces 96,98. In certain embodiments, the assembly process is performed within about 5 to 30 minutes after the treatment process, which is a sufficient period of time to assemble the members 86,88 together before the oxygen rich layers formed on the surfaces 96,98 begin to decay.

In an alternative embodiment, the outer tubular member 88 is pre-assembled over the inner tubular member 86, and the outer tubular member 88 is pulled over itself inside-out along a length of the assembly, exposing a portion of the interior surface 96. The exposed exterior surface 98 of the inner tubular member 86 and the interior surface 96 of the outer tubular member 88 are then simultaneously subjected to a gas plasma treatment within the treatment chamber 16. Following the plasma treatment, the outer tubular member 88 is then rolled back so that the modified interior surface 98 of the outer tubular member 88 contacts the modified exterior surface 96 of the inner tubular member 86 to directly bond the two surfaces 96,98 together.

In those embodiments in which the assembly is performed after treatment and the outer tubular member 88 comprises a silicone elastomer, a swelling solution such as hexane/heptane may be applied to the outer tubular member 88 (block 116), causing the inner diameter of the member 88 to increase in size, which in turn, facilitates insertion of the outer tubular member 88 over the inner tubular member 86. Alternatively, and in other embodiments, pressurized inert gas can be admitted through the interior lumen of the outer tubular member 88, causing the inner diameter of the modified outer tubular member 88 to increase in size.

Next, at block 118, the outer tubular member 88 is placed over the inner tubular member 86 such that the inner lumen of the outer tubular member 88 overlaps the inner tubular member 86. Then, as the effect of the swelling solution dissipates, the inner diameter of the outer tubular member 88 decreases to its initial, pre-swelling size, resulting in conformal contact between the outer surface 96 of the inner tubular member 86 and the inner surface 98 of the outer tubular member 88. When this occurs, the oxygen rich layers formed on the inner and outer surfaces 96,98 contact each other, forming a direct bond between the tubular members 86,88 (block 120). The treatment and assembly process can then be repeated one or more times for each additional outer tubular member 88 to be assembled over the inner tubular member 86.

Although the inner and outer tubular members 86,88 may each comprise a silicone containing elastomer such as silicone rubber, in other embodiments other types of polymeric materials may be employed. In some embodiments, for example, the outer tubular member 88 may comprise a silicone containing elastomer such as polydimethylsiloxane (PDMS), or PDMS containing polymers such as fluorosilicones or polyurethanes, whereas the inner tubular member 86 can comprise any elastomeric, thermoplastic or rigid polymer with a suitably modified surface such as those containing silanol or hydroxyl functionality capable of reacting with surface oxidized silicone containing elastomers. In some embodiments, the inner tubular member 86 includes a biocompatible metal containing a glass coating on the outer surface 96, whereas the outer tubular member 88 is a plasma treated silicone containing elastomer in a compression fit with the inner tubular member 86.

EXAMPLE

Several operational parameters of the gas plasma treatment apparatus 10 were experimented with to determine their influence on the bonding properties of several silicone test specimens bonded together. In one illustrative experiment, a number of silicone outer and lead body tubes were subjected to separate cold gas plasma treatments at an oxygen flow rate of 200 sccm and a power rate of 50 Watts each. Such experiments included exposing the silicone tubing to oxygen plasma under near vacuum pressures (e.g., from 70 to 20 mTorr). The outer silicone tube, which comprised an outer tubular member of the bonded assembly, was subjected to the cold gas plasma treatment for a period of 10 minutes. The lead body tube, which comprised an inner tubular member of the bonded assembly, in turn, was subjected to the cold gas plasma treatment for a period of 1 minute. Once treated, the outer tube and lead body tube specimens were then stored in air. Each of the outer tubes were then subjected to a Heptane soak. In some instances, the lead body tubing specimens were placed within the inner lumen of the outer tube specimens immediately after plasma exposure. In other instances, the lead body tube specimens were placed within the inner lumen of the outer tube specimens about 30 minutes after plasma exposure.

Pull and peel testing was then performed to determine the structural integrity of the direct bond formed between each of the bonded test specimens. The bonding dwell time ranged from about 30 minutes to 24 hours under ambient conditions before the bonded test specimens were subjected to mechanical testing to determine the structural integrity of the bond. In one pull test, several bonded silicone tubing assemblies with approximately a 3-inch overlap were pulled at a rate of approximately 10 inches/minute, which resulted in tubing failure at a force of about 3.5 lbs and significant elongation;

nearly a ten-fold increase compared to several non-bonded assemblies. Similarly, bonded silicone tubing assemblies showed a peel force of over 1 lb at a peel rate of 10 inches/minute and failure within the outer tube, as compared to non-bonded specimens which exhibited no peel adhesion. Those test specimens that were bonded together immediately after the surface treatment did not exhibit bond failure, but instead resulted in the failure of the tubing. In contrast, those test specimens that were bonded together 30 minutes subsequent to the surface treatment exhibited bond failure at the bonding interface between the outer tube and the lead body tube.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A medical lead, comprising
an outer tubular member formed at least in part of silicone and having an inner surface, an outer surface, and an interior lumen, the inner surface of the outer tubular member subjected to a oxidative cold gas plasma treatment;
an inner tubular member formed at least in part of silicone and having an outer surface, the outer surface of the inner member subjected to an oxidative cold gas plasma treatment; and
wherein an overlapping region between the inner surface of the outer tubular member and the outer surface of the inner member forms a direct bond between the inner and outer members when the inner member is in a compression fit with the outer tubular member.

2. The medical lead of claim 1, wherein the inner and outer members are directly bonded together without an adhesive.

3. The medical lead of claim 1, wherein the inner member comprises an elongate tubular member including at least one interior lumen.

4. The medical lead of claim 1, wherein the inner member has a length, and wherein the overlapping region between the inner and outer members extends along a portion of the length.

5. The medical lead of claim 1, wherein the inner member comprises a silicone containing polymer.

6. The medical lead of claim 1, wherein the inner member comprises a metal including a glass coating.

7. The medical lead of claim 1, wherein the outer tubular member comprises a silicone containing elastomer.

8. A method of manufacturing a medical device lead, the method comprising:
subjecting an inner surface of at least a portion of a first elongate, silicone tubular member to an oxidative cold gas plasma treatment for a first period of time, the oxidative cold gas plasma treatment adapted to modify the inner surface of the first elongate tubular member with an oxygen rich layer;
subjecting an outer surface of at least a portion of a second elongate, silicone tubular member to an oxidative cold plasma treatment for a second period of time, the oxidative cold gas plasma treatment adapted to modify the outer surface of the second elongate tubular member with an oxygen rich layer; and
assembling the first elongate tubular member over the second elongate tubular member after subjecting the outer and inner surfaces to the oxidative cold gas plasma treatments, wherein a direct bond is formed along an overlapping region between the first and second elongate tubular members.

9. The method of claim 8, wherein the first elongate tubular member includes an outer tube.

10. The method of claim 8, wherein the first elongate tubular member comprises a silicone containing elastomer.

11. The method of claim 8, wherein the second elongate tubular member comprises a silicone containing polymer.

12. The method of claim 8, wherein the second elongate tubular member comprises a metal including a glass coating.

13. The method of claim 8, wherein the second elongate tubular member includes a lead body tube.

14. The method of claim 8, wherein the at least one first elongate tubular member includes a plurality of tubular members, and further including assembling each of the first elongate tubular members in a compression fit over the second elongate tubular member, wherein a direct bond is formed along an overlapping region between the second elongate tubular member and each of the first elongate tubular members.

15. The method of claim 8, wherein the first period of time is greater than the second period of time.

16. The method of claim 15, wherein the first period of time is between about 5 minutes to 15 minutes.

17. The method of claim 15, wherein the second period of time is between about 30 seconds to 2 minutes.

18. The method of claim 8, wherein assembling the first elongate tubular member over the second elongate tubular member includes applying a swelling solution to the first elongate tubular member.

19. The method of claim 8, wherein subjecting an inner surface of at least a portion of the first elongate tubular member to an oxidative cold gas plasma treatment includes subjecting an entire length of the first elongate tubular member to the cold gas plasma treatment.

20. The method of claim 8, wherein the first elongate tubular member is assembled over the second elongate tubular member within a period of about 30 minutes after subjecting the outer and inner surfaces to the oxidative cold gas plasma treatments.

21. The method of claim 8, wherein the second elongate tubular member has a length, and wherein the overlapping region between the first and second elongate tubular members extends along a portion of the length.

22. The method of claim 8, wherein the direct bond along the overlapping region is an adhesiveless bond.

* * * * *